US009187195B2

(12) United States Patent
de Bruin et al.

(10) Patent No.: US 9,187,195 B2
(45) Date of Patent: Nov. 17, 2015

(54) PROCESS FOR MAKING PERFORATIONS IN A PLASTIC FILM MATERIAL

(75) Inventors: Martijn Willem de Bruin, Kockengen (NL); Bastian Rinke Antony Groeneweg, Rockanje (NL)

(73) Assignee: Perfotec B.V., Mijdrecht (NL)

( * ) Notice: Subject to any disclaimer, the term of this patent is extended or adjusted under 35 U.S.C. 154(b) by 809 days.

(21) Appl. No.: 12/989,964

(22) PCT Filed: Apr. 29, 2008

(86) PCT No.: PCT/EP2008/003446
§ 371 (c)(1),
(2), (4) Date: Nov. 24, 2010

(87) PCT Pub. No.: WO2009/132663
PCT Pub. Date: Nov. 5, 2009

(65) Prior Publication Data
US 2011/0056346 A1 Mar. 10, 2011

(51) Int. Cl.
B28B 1/48 (2006.01)
B65B 25/04 (2006.01)
B23K 26/03 (2006.01)
B23K 26/38 (2014.01)
B23K 26/40 (2014.01)
B65B 57/00 (2006.01)
B65B 61/02 (2006.01)
G01N 15/08 (2006.01)

(52) U.S. Cl.
CPC ............... B65B 25/04 (2013.01); B23K 26/03 (2013.01); B23K 26/381 (2013.01); B23K 26/4065 (2013.01); B65B 57/00 (2013.01); B65B 61/02 (2013.01); G01N 15/088 (2013.01); G01N 2015/0833 (2013.01); G01N 2015/0846 (2013.01); Y10T 83/04 (2015.04)

(58) Field of Classification Search
USPC ......... 264/154, 504, 509, 119, 284, 293, 413, 264/155, 156
See application file for complete search history.

(56) References Cited

U.S. PATENT DOCUMENTS

| 4,218,606 | A | 8/1980 | Whitman, III | |
| 5,365,033 | A * | 11/1994 | Williams | 219/121.71 |
| 6,441,340 | B1 | 8/2002 | Varriano-Marston | |
| 6,730,874 | B2 | 5/2004 | Varriano-Marston | |
| 7,083,837 | B1 | 8/2006 | Varriano-Marston | |
| 2003/0029850 | A1* | 2/2003 | Varriano-Marston | 219/121.71 |

FOREIGN PATENT DOCUMENTS

| DE | 102 51 610 A1 | 5/2004 |
| EP | 0351115 | 1/1990 |
| FR | 2 873 992 A | 2/2006 |
| WO | 9322207 | 11/1993 |
| WO | WO 02/12068 A | 2/2002 |
| WO | WO 2006/063609 A | 6/2006 |

OTHER PUBLICATIONS

International Search Report mailed Jan. 28, 2009 by the European Patent Office, The Hague, Netherlands.
Article C. Sanz et al., Quality of Strawberries Packed With Perforated Polypropylene, Journal of Food Science, vol. 64, No. 4, 1999.
Article Svetlana Fishman et al., Mathematical Model for Perforation Effect on Oxygen and Water Vapor Dynamics in Modified-Atmosphere Packages, Journal of Food Science, vol. 61, No. 5, 1996.
Article J.P. Emond et al., Mathematical Modeling of Gas Concentration Profiles in Modified Atmosphere Bulk Packages, 1998 American Society of Agricultural Engineers 0001-2351 / 98 / 4104-1075.
Article Errol W. Hewett et al., Modified Atmosphere Storage and Bitter Pit Reduction in Cox's Orange Pippin' Apples, Scientia Horticulturae, 39 (1989) 117-129.
Article Sudheer R. Kona et al., A Robust Algorithm for Detecting Pinholes in Transparent Plastic Films, Pattern Recognition, vol. 26, No. 8. pp. 1215, 1227, 1993.
Article T.J. Mathhams et al., Mechanical Properties of Long-Fibre Thermoplastic Composites With Laser Drilled Microperforations 1. Effect of Perforations in Consolidated Material, Composites Science and Technology 59 (1999) 1169-1180.
Article T.J. Mathhams et al., Mechanical Properties of Long-Fibre Thermoplastic Composites With Laser Drilled Microperforations 2. Effect of Prior Plastic Strain, Composites Science and Technology 59 (1999) 1181-1187.
Article Dong Sun Lee et al., Using Pinholes as Tools to Attain Optimum Modified Atmospheres in Packages of Fresh Produce, Packaging Technology and Science 11, 119-130 (1998).
Machine translation of DE 10251610 A1 (Grosse Werner).
Machine translation of FR 2 873 992 A (Sud Perle Soc Par Actions Simp).

* cited by examiner

Primary Examiner — Stella Yi
(74) Attorney, Agent, or Firm — Mendelsohn, Drucker and Dunleavy, P.C.

(57) ABSTRACT

A process for making perforations in a plastic film material to be used in a package for products prone to decay, in which the surface area of the perforations made in a defined surface area of the plastic film material must have a predetermined value, which process has the following steps: A. making of one perforation or a number of perforations in the defined surface area of the plastic film material, B. measuring the surface area of the perforation or of the number of perforations made in step A, C. calculating the difference between the predetermined perforation value minus the surface area of all perforations present in the defined surface area, D. if the difference is smaller than a first predetermined reference value, stopping the making of perforations in the defined surface area of the plastic film material, or if the difference is larger than the first predetermined reference value repeating the steps A to C until the difference is at most equal to the first predetermined reference value.

17 Claims, No Drawings

PROCESS FOR MAKING PERFORATIONS IN A PLASTIC FILM MATERIAL

PRIORITY CLAIM TO RELATED APPLICATIONS

This application is a national stage application under 35 U.S.C. §371 of PCT/EP2008/003446, filed Apr. 29, 2008, published as WO 2009/132663 A1 on Nov. 5, 2009, which application and publication is incorporated herein by reference and made a part hereof in its entirety.

The invention relates to a process for making perforations in a plastic film material to be used in a package for products prone to decay, in which the surface area of the perforations made in a defined surface area of the plastic film material must have a predetermined value.

Such a process is known from EP-A-1 332 089.

According to this known process the total surface area of the perforations per package is defined based upon the type and quantity of products to be packed. Based upon that information, the perforation device, such as a laser beam perforator is controlled in such a way that the number of perforations and the surface of each perforation results in the total perforated surface area to be obtained per package.

By means of this process relatively good results have been obtained although is was not optimal. This is due to the fact that it is accepted that by controlling the perforating device in a defined way a perforation of a defined shape and surface area will be obtained. In practice it has been found that this is not correct. In a number of situations the perforating device fails to work completely according to expectations which is especially the case with the commonly used laser beam perforating devices. In other situations the shape or surface area of the perforation is different from the expected shape and surface area as set by the control system. This can be due to different reasons, such as a deviation in the plastic film material quality, fluctuations in the speed of movement of the plastic film material during the perforating action and variations in the perforating performance of the perforating device itself, for instance as caused by intensity variation of the laser beam.

It is therefore an object of the invention to provide a process of the above identified type in which the total surface area of the perforations is more accurately controlled than in the known process.

This object is achieved by means of a process having the following steps:
A. making of one perforation or a number of perforations in the defined surface area of the plastic film material,
B. measuring the surface area of the perforation or of the number of perforations made in step A,
C. calculating the difference between the predetermined perforation value minus the surface area of all perforations present in the defined surface area,
D. if the difference is smaller than a first predetermined reference value, stopping the making of perforations in the defined surface area of the plastic film material, or if the difference is larger than the first predetermined reference value repeating the steps A to C until the difference is at most equal to the first predetermined reference value.

In this way it becomes possible to check the real surface area of the perforation or perforations made in the plastic film material and thereby obtain the right perforation value in the package.

The surface area of each perforation made can be measured in different ways. A convenient way for doing so is to make a photographic picture of each perforation made and based upon that to calculate the surface area of that perforation. This value can be stored in an digital electronic calculating and control device. Another way is to compare the photographic picture of the perforation with a number of standard perforations stored in the calculating device and based upon that comparison define which standard perforation is the closest to the photographic picture of the perforation made which automatically defines the surface area of the perforation made as being equal to the surface area of the selected standard perforation. The surface areas of all perforations made in the defined surface area of the plastic film material are added in the digital calculating device and also compared to the predetermined value. This value is defined based upon the type and quantity of products to be present in the package and is in fact based upon the measurement of the respiration of the product itself before this product will be packed. In the known process the definition of film permeability and surface area of micro perforations is based upon average theoretical respiration values. However it is proven that the real respiration values can differ with more than 50% during the seasons. So it is necessary to base the surface area of the perforations upon measurement of the actual respiration of the products.

The defined surface area of the plastic film material can be either any reference value which can be used, such a one square meter or the like, or it can be the total surface area of plastic film material to be used in each individual package. If needed this value can be corrected in view of the portion of the plastic film material in the package which cannot be in contact with the products in the package. In fact this means the surface area of plastic film material which actually separates the products from the environment. In this way some parts are excluded out of the total surface area of the film material used such as parts used as a hand grip or outside of the seams which cannot contribute in the exchange of air between the interior and the exterior of the package. In other cases it is also possible to take into account the part of the surface area which is in fact covered by a tray or the like as frequently used in such packages for supporting the products.

In the digital electronic processor the difference between the surface area of all perforations made in the defined surface area of the plastic film material is deducted from the predetermined value of the required total surface area of the perforations and this difference is compared to a first predetermined reference value. This first predetermined reference value may be zero or a value very close to zero, corresponding for instance to the smallest possible perforation which can be practically made by the perforating device used.

If the difference is larger than that first predetermined value, one or more additional perforations can be made in the same defined surface area and the calculation process is repeated until the difference is lower that the first predetermined reference value. IN order to obtain a difference of almost zero, the additional perforations made may have a smaller surface area, which may be done by controlling the perforation device in the right way. Whether or not perforations with reduced surface area are made can be made dependent upon a second comparison with a second predetermined reference value. As soon as the difference becomes smaller than that value perforations with a reduced surface area will be made. As long as the difference is bigger than that second value perforations with a standard setting of the perforating device are made.

It is common practice to use perforations in this type of packages which have a general circle shape with a diameter between 10 and 250 micrometer. The size and shape of the perforation is dependent upon the perforating device. In case of a laser beam system the diameter is controlled by the intensity of the laser beam. The shape may be round but due to the speed of the plastic film material along the perforating device, this shape may become more oval.

In the above disclosed approach it is accepted that the surface area of each perforation is measured and used for calculations. In a convenient process it may also be done in such a way that not all the perforations are measured, but that with a defined interval either in time or in distance a perforation is measured. This allows a less complicated electronic device to be used, as the speed of processing can be substantially reduced.

The above disclosed approach is also completely based upon the assumption that the total surface area of all perforations effectively present in the package define the air transfer rate (ATR) between the interior and the exterior of the package. In practice this is not completely correct in that the ATR through a perforation is directly related to the surface area of that perforation, which means that the ATR through one big perforation is larger than through a number of small perforations with the same surface area of the big perforation. This is partly due to transition effects taking place at the edges of the perforations and may also be dependent upon the quality of the edges, for instances straight edges compared to irregularly shaped edges.

In order to improve the accuracy of the perforating system the digital calculating system can be designed in such a way that for the comparison of the required surface area of the perforations and the predetermined value of the surface area of the perforations the ATR is used as a correction factor so that a more reliable value is obtained.

In an article written by V. Ghosh and R. C. Anantheswaran: Oxygen Transmission Rate Through Micro-perforated Films: Measurement and Model Comparison, published in Journal of Food Process Engineering 24 (2001), pages 113-133 it has been disclosed that it is not the Air Transmission Rate (ATR), but the Oxygen Transmission Rate (ORT) which is responsible for the conservation of food products, especially vegetables packed in plastic film material such as bags or trays. The OTR may be directly related to the ATR, as the oxygen content of the air is almost constant. However small fluctuations can occur which are mostly due to local circumstances, such as temperature and humidity. In view thereof it may be advantageous to use the OTR-value in stead of the ATR as a correction factor for the calculation of the perforated surface area. For this purpose use can be made of the mathematical models disclosed in the above cited article, Further background for this can be found in an article of Nazir Mir and Randolph M. Beaudry with the title Modified Atmosphere Packaging.

In a number of situations it may even be advisable to use another parameter which is called the Moisture Volume Transfer Rate (MVTR), which is also very often dependent on local circumstances, but which combined with the OTR will lead to optimal results.

Up till now it was accepted that the ATR, OTR or MVTR is completely defined by the perforations made in the plastic film material. In reality each plastic film material has a basis ATR, OTR and MVTR which is dependent upon the composition of the film material and its thickness. As a rule these values of the green film material are generally known to the supplier of the film material and it is possible to adjust the complete process of making perforations by taking into account these green values of the film material. By introducing these green values in the digital electronic calculator it becomes possible to adjust the complete calculation and thereby optimize the number and size of perforations.

It is obvious that the invention is not restricted to the described embodiments, but that within the scope of the claims modifications can be applied without departing from the inventive concept. So it is possible to use a single perforating device which means that all perforations are located on one single line, but otherwise more than one perforating device may be used as well whereby a more uniform distribution of the perforations can be obtained.

The invention claimed is:

1. A process for making perforations in a plastic film material to be used in a package for products prone to decay, in which a surface area of the perforations made in a defined surface area of the plastic film material must have a predetermined perforation value, the process comprising steps:
   A. making one perforation or a number of perforations in the defined surface area of the plastic film material,
   B. measuring the surface area of the perforation or of the number of perforations made in step A,
   C. calculating the difference between the predetermined perforation value minus the surface area of all perforations present in the defined surface area,
   D. if the difference is smaller than a first predetermined reference value, stopping the making of perforations in the defined surface area of the plastic film material, or if the difference is larger than the first predetermined reference value repeating the steps A to C until the difference is at most equal to the first predetermined reference value, and
   E. if the difference is smaller than a second predetermined reference value but larger than the first predetermined reference value, steps A to C are repeated but the surface area of the perforation or of the number of perforations is made smaller.

2. A process according to claim 1, wherein the defined surface area of the plastic film material is equal to a total surface area of plastic film material used in one said package.

3. A process according to claim 1, wherein the defined surface area of the plastic film is equal to a total surface area of plastic film material which in an ultimate package may come into contact with contents of the package.

4. A process according to claim 1, wherein the measured surface area of the perforation or of the number of perforations is adjusted taking into account an air transfer rate (ATR) based upon a shape and surface area of each individual perforation.

5. A process according to claim 1, wherein the predetermined perforation value is expressed as an oxygen transmission rate (OTR)-value and/or moisture volume transfer rate (MVTRU)-value and the measured surface area of the perforations in the defined surface area of the plastic film material is also converted into an OTR-value and/or MVTR-value.

6. A process according to claim 5, wherein the OTR-value and/or MVTR-value of the plastic film material as such is used for correcting the calculation of the difference.

7. A process according to claim 5, wherein the OTR-value and/or MVTR-value of any other material used in the ultimate package and which may be in contact with the products in the package is used for correcting the calculation of the difference.

8. A process according to claim 1, wherein the perforations are made by at least one laser beam.

9. A process according to claim 8, wherein an intensity of at least one laser beam is controlled as a function of the calculated difference.

10. A process according to claim 1, wherein the predetermined value of the surface area of the perforation or the number of perforations in the defined surface area of the plastic film material is based upon a measurement of a respiration of a product to be packaged.

11. A process according to claim 4, wherein an OTR-value and/or an MVTR-value of the plastic film material as such is used for correcting the calculation of the difference.

12. A process according to claim 4, wherein an OTR-value and/or an MVTR-value of any other material used in an ultimate package and which may be in contact with the products in the package is used for correcting the calculation of the difference.

13. A process for making perforations in a plastic film material to be used in a package for products prone to decay, in which a surface area of the perforations made in a defined surface area of the plastic film material must have a predetermined perforation value, the process comprising steps:
   A. making one perforation or a number of perforations in the defined surface area of the plastic film material,
   B. measuring the surface area of the perforation or of the number of perforations made in step A,
   C. calculating the difference between the predetermined perforation value minus the surface area of all perforations present in the defined surface area,
   D. if the difference is smaller than a first predetermined reference value, stopping the making of perforations in the defined surface area of the plastic film material, or if the difference is larger than the first predetermined reference value repeating the steps A to C until the difference is at most equal to the first predetermined reference value, and
   E. if the difference is smaller than a second predetermined reference value but larger than the first predetermined value, steps A to C are repeated but the surface area of the perforation or of the number of perforations is made smaller and wherein step B comprises the steps of:
   B1. making at least one photographic picture of one or more perforations made, and
   B2. determining the surface area of each said perforation made based on the at least one photographic picture made in step B1.

14. A process according to claim 13, wherein the defined surface area of the plastic film material is equal to a total surface area of plastic film material used in one said package.

15. A process according to claim 13, wherein the defined surface area of the plastic film is equal to a total surface area of plastic film material which in an ultimate package may come into contact with contents of the package.

16. A process according to claim 13, wherein step B2 further comprises calculating a surface area of one said perforation pictured in the photograph based upon the photographic picture of that perforation.

17. A process according to claim 13, wherein step B2 further comprises determining the surface area of one said perforation pictured in the photograph from a comparison of the photographic picture of that perforation with a number of standard perforations and based upon that comparison identifying which standard perforation is closest to the photographic picture of the one said perforation and defining a surface area of the one said perforation as being equal to a surface area of the identified closest standard perforation.

\* \* \* \* \*